United States Patent
Okano et al.

(10) Patent No.: US 12,109,341 B2
(45) Date of Patent: Oct. 8, 2024

(54) DISCHARGE DEVICE

(71) Applicant: SHARP KABUSHIKI KAISHA, Sakai (JP)

(72) Inventors: Satoshi Okano, Sakai (JP); Nobuyuki Ohe, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 169 days.

(21) Appl. No.: 17/975,574

(22) Filed: Oct. 27, 2022

(65) Prior Publication Data
US 2023/0149591 A1    May 18, 2023

(30) Foreign Application Priority Data

Nov. 17, 2021    (JP) ................. 2021-187086

(51) Int. Cl.
*A61L 9/22* (2006.01)
*B03C 3/82* (2006.01)
*H01T 23/00* (2006.01)

(52) U.S. Cl.
CPC ..... *A61L 9/22* (2013.01); *B03C 3/82* (2013.01); *H01T 23/00* (2013.01)

(58) Field of Classification Search
CPC .. A61L 9/22; A61L 2209/10; A61L 2209/211; A61L 2209/212; A61L 9/015; B03C 3/82; H01T 23/00; H01T 19/00; H01T 19/04; F24F 8/30; F24F 2221/36; C01B 13/11
USPC ...................................................... 361/229
See application file for complete search history.

(56) References Cited

U.S. PATENT DOCUMENTS

| | | | |
|---|---|---|---|
| 2014/0103793 A1* | 4/2014 | Nishida | H01T 19/04 313/231.71 |
| 2016/0211654 A1* | 7/2016 | Sekoguchi | H01T 23/00 |
| 2016/0218490 A1* | 7/2016 | Nishida | A61L 9/22 |
| 2021/0012995 A1* | 1/2021 | Okano | H01J 27/022 |

FOREIGN PATENT DOCUMENTS

| | | | | |
|---|---|---|---|---|
| WO | WO-2014203562 A1 | * | 12/2014 | H01J 27/022 |
| WO | WO-2015151309 A1 | * | 10/2015 | B03C 3/38 |
| WO | WO-2018055783 A1 | * | 3/2018 | H01T 23/00 |
| WO | WO-2018055789 A1 | * | 3/2018 | H01T 19/04 |

OTHER PUBLICATIONS

WO 20180557; Discharge Device and Electric Device; Figures and Entire specification (Year: 2019).*

* cited by examiner

*Primary Examiner* — Dharti H Patel
(74) *Attorney, Agent, or Firm* — ScienBiziP, P.C.

(57) ABSTRACT

A discharge device is housed in a housing portion of a holder. The discharge device includes a housed section and a discharge electrode protruding from the housed section. The housed section is housed in the housing portion. The housed section includes a bottom wall and two side walls. The two side walls oppose each other in a longitudinal direction of the bottom wall. At least one of the two side walls is connected to the bottom wall via a curved surface. The curved surface guides a corner of the housing portion when the housed section is housed in the housing portion. As a result, the housed section is housed in the housing portion without catching on the corner.

11 Claims, 7 Drawing Sheets

DISCHARGE DEVICE

CROSS-REFERENCE TO RELATED APPLICATIONS

This application claims the benefit of priority to Japanese Patent Application Number 2021-187086 filed on Nov. 17, 2021. The entire contents of the above-identified application are hereby incorporated by reference.

BACKGROUND

Technical Field

The disclosure relates to a discharge device.

WO 2018/055783 discloses a discharge device configured to generate a discharge product from an electrode. The discharge device is attached to a holder provided inside an electronic apparatus. The discharge device can be attached to the holder by simply fitting the discharge device into a predetermined portion of the holder.

SUMMARY

While the discharge device of WO 2018/055783 can be easily attached to the holder, there is room for improving the structure to allow for easier attachment.

The disclosure has been made in view of the issue described above, and an object thereof is to provide a discharge device that can be easily attached to a holder.

According to an aspect of the disclosure, a discharge device is housed in a housing portion of a holder. The discharge device includes a housed section and a discharge electrode protruding from the housed section. The housed section is housed in the housing portion. The housed section includes a bottom wall and two side walls. The two side walls oppose each other in a longitudinal direction of the bottom wall. At least one of the two side walls is connected to the bottom wall via a curved surface. The curved surface guides a corner of the housing portion when the housed section is housed in the housing portion. As a result, the housed section is housed in the housing portion without catching on the corner.

According to the disclosure, it is possible to provide a discharge device that can be easily attached to a holder.

BRIEF DESCRIPTION OF DRAWINGS

The disclosure will be described with reference to the accompanying drawings, wherein like numbers reference like elements.

DESCRIPTION OF EMBODIMENTS

Figure 1:
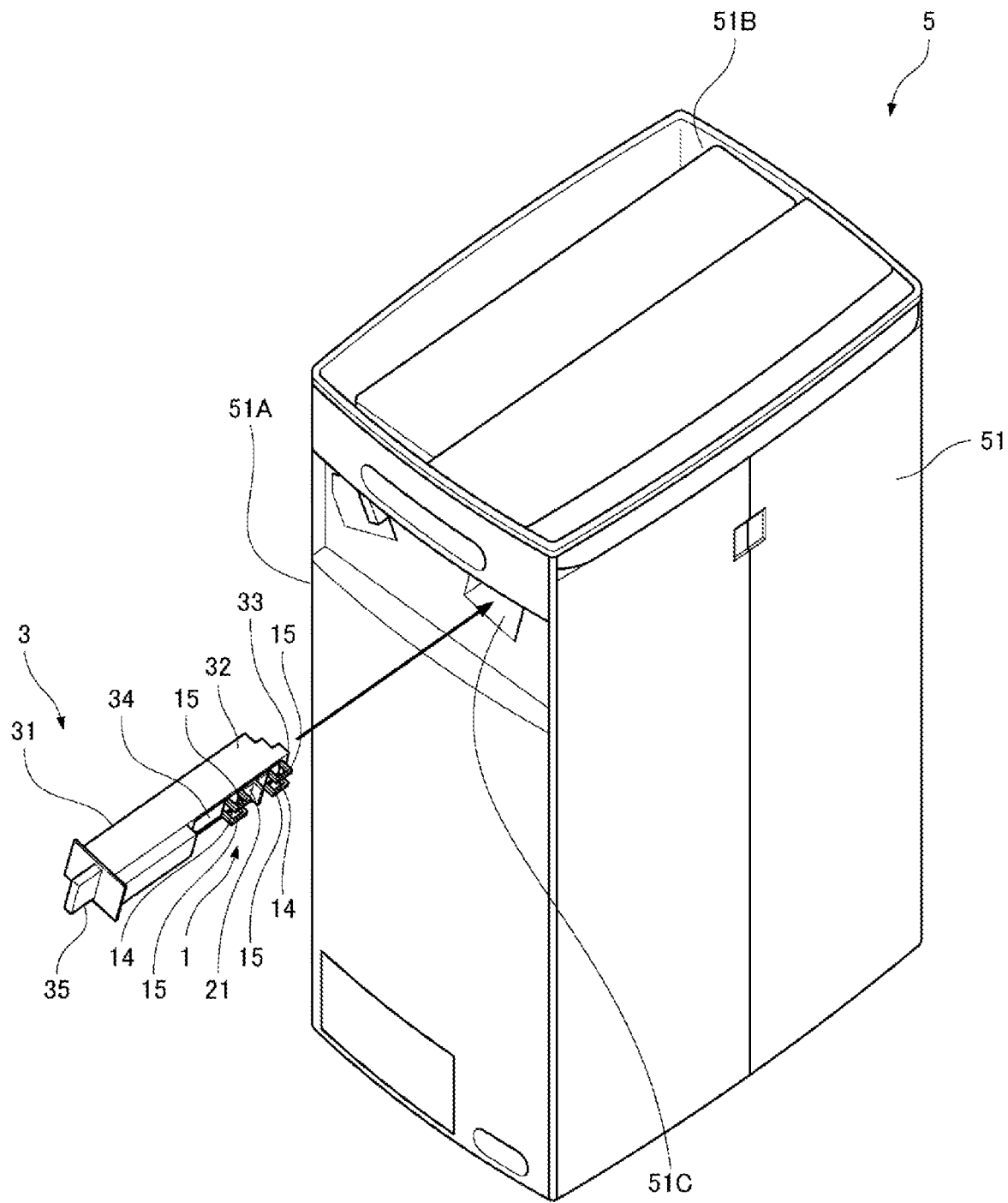
FIG. 1 is a perspective view illustrating an electronic apparatus including a discharge device according to an embodiment of the disclosure.

Embodiments of the disclosure will be described hereinafter with reference to the accompanying drawings. Note that, in the drawings, the same or equivalent components are denoted by the same reference signs and description thereof will not be repeated.

Before describing a discharge device 1 of the disclosure, an electronic apparatus 5 including the discharge device 1 of the disclosure will be described. FIG. 1 is a perspective view illustrating the electronic apparatus 5 including the discharge device 1 according to an embodiment of the disclosure.

The electronic apparatus 5 illustrated in FIG. 1 includes a blower function and a function of generating a discharge product. In addition to the functions described above, the electronic apparatus 5 may also include a function of changing the physical property of air. The blower function is a function of intaking air around the electronic apparatus 5 into the electronic apparatus 5, and sending out the in-taken air to the outside of the electronic apparatus 5. The function of generating a discharge product includes, for example, a function of suppressing the action of bacteria by generating ions or free radicals. The function of changing the physical property of air includes, for example, a function of removing particles in the air. Specifically, the electronic apparatus 5 having the blower function and the function of generating a discharge product into the air is a discharge product generator such as an ion generator or an ozone generator. As a discharge product generator with the function of removing particles contained in the air, the electronic apparatus 5 is an air purifier with a discharge product generating function. The electronic apparatus 5 may include, in addition to an air purifier with a discharge product generating function, a humidifying air purifier with a discharge product generating function, and a humidifying/dehumidifying air purifier with a discharge product generating function.

The electronic apparatus 5 includes a main body 51, a holder 3, and the discharge device 1. The discharge device 1 is attached to the holder 3, and the holder 3 is disposed inside the main body 51, which has a box shape.

Electrical components (not illustrated) for operating the electronic apparatus 5 are housed in the main body 51. A voltage is applied to the electrical components via a power supply cable (not illustrated) provided outside the main body 51, and a feeder connector (not illustrated) provided inside the main body 51.

An inlet port 51A for sucking air present outside the main body 51 is provided in a side surface of the main body 51. The air taken into the main body 51 from the inlet port 51A passes through a ventilation passage (not illustrated) provided inside the main body 51, and is sent out to the outside of the main body 51 from an outlet port 51B formed in the top surface of the main body 51.

Further, a holder insertion port 51C that allows the inside and the outside of the main body 51 to communicate is formed in a side surface of the main body 51. A space inside the main body 51 communicating with the holder insertion port 51C communicates with the ventilation passage mentioned above. A feeder connector is disposed in this space.

A voltage is applied to the discharge device 1 through the feeder connector, so that a discharge product is generated. Examples of the discharge product generated by the discharge device 1 include ions or free radicals. Examples of the ions include a positive ion (for example, $H^+(H_2O)_m$, where m is any integer), a negative ion (for example, $O^{2-}(H_2O)_n$, where n is any integer), or a combination of these ions. Examples of the free radicals include a hydroxyl radical (—OH), a hydrogen radical (—H), an oxygen radical (—O), a hydroperoxyl radical (—$HO_2$), hydrogen peroxide ($H_2O_2$), and ozone ($O_3$). The discharge product has, for example, an effect of suppressing the action of bacteria and suppressing harmful effects of the bacteria on the human body.

The discharge device 1 is housed in and held by the holder 3, thereby being attached to the holder 3. The discharge device 1 attached to the holder 3 is inserted into the main body 51 through the holder insertion port 51C. The discharge device 1 inserted into the main body 51 is connected to the feeder connector, and is arranged such that part of the discharge device 1 is exposed on the ventilation passage. The holder 3, in which the discharge device 1 is arranged as described above, is held in the main body 51. A voltage is applied to the discharge device 1 connected to the feeder connector. By arranging the discharge device 1 on the ventilation passage, the discharge product is dispersed into the air passing through the ventilation passage. As a result, the discharge product is sent out to the outside of the main body 51 and suppresses the action of bacteria present outside the main body 51.

Figure 2:
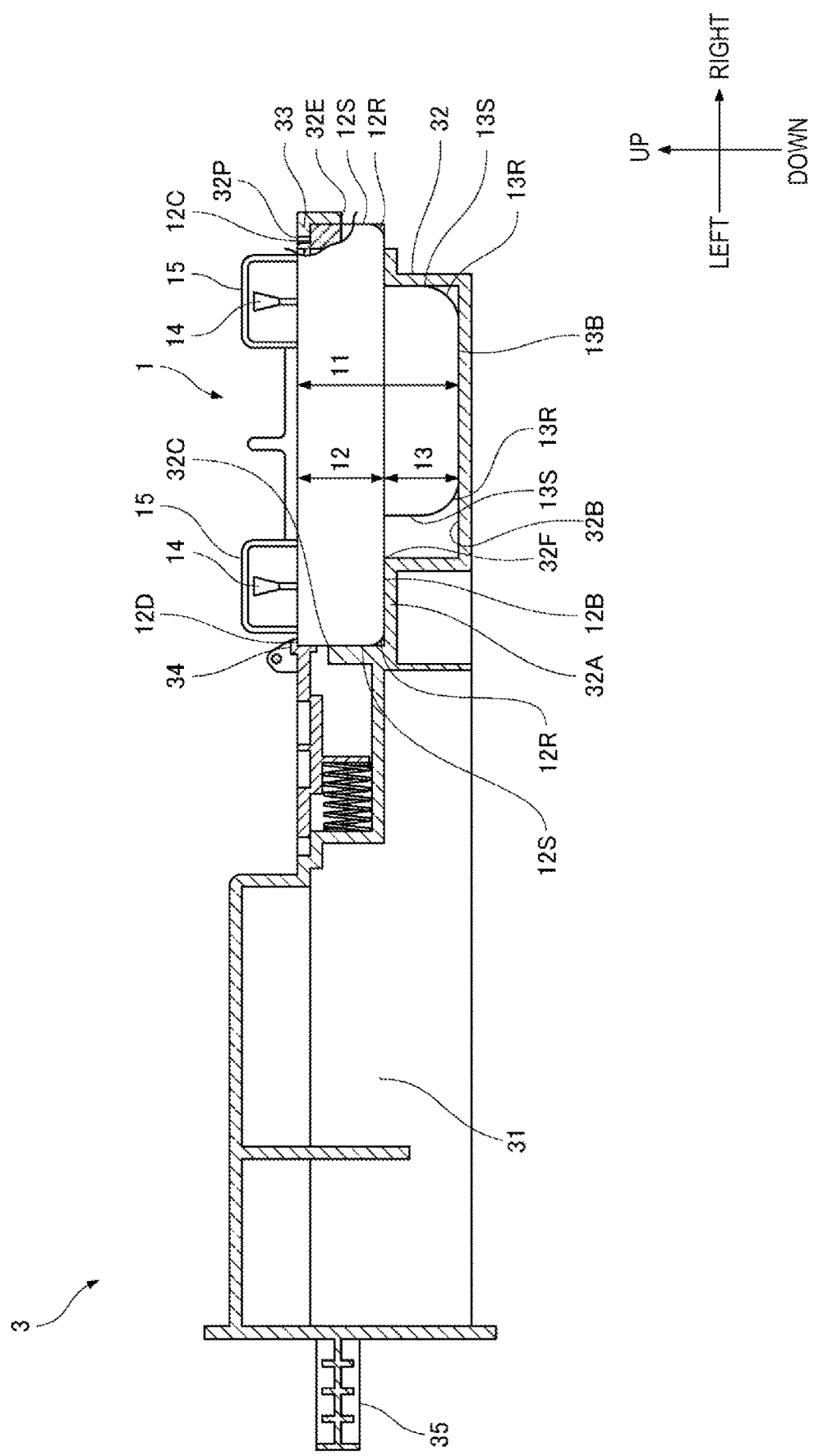
FIG. 2 is a cross-sectional view of a holder to which the discharge device according to the embodiment of the disclosure is attached.

Referring to FIG. 2, the holder 3 to which the discharge device 1 of the disclosure is to be attached will be described below. FIG. 2 is a cross-sectional view of the holder 3 to which the discharge device 1 according to the embodiment of the disclosure is attached.

As illustrated in FIG. 2, the holder 3 includes a holder base 31, a housing portion 32, a first securing portion 33, a second securing portion 34, and a holder handle 35. Hereinafter, in the description of the holder 3, the directions illustrated in FIG. 2 are defined as up-down and left-right directions for convenience. That is, the longitudinal direction of the holder 3 is defined as the left-right direction. The direction orthogonal to the left-right direction is defined as the up-down direction.

The holder base 31 is a portion for setting a position of the housing portion 32, in which the discharge device 1 is housed, with respect to the main body 51. The housing portion 32 has a box shape. The housing portion 32 is provided at a right end portion of the holder base 31. By appropriately setting the length of the holder base 31 in the left-right direction, the discharge device 1 housed in the housing portion 32 is partially disposed in the ventilation passage, and the discharge device 1 is connected with the feeder connector.

A discharge device housing port 32P open in the up-down direction is formed in the upper portion of the housing portion 32. The discharge device housing port 32P allows the inside and the outside of the housing portion 32 to communicate with each other. The discharge device 1 passes through the discharge device housing port 32P to move in or out of the housing portion 32.

A bottom surface 32B is provided inside the housing portion 32. The interior of the housing portion 32 has a step structure in which a step 32A is provided. The step 32A is provided such that the lower side of the housing portion 32 provided with the step 32A has a small dimension in the left-right direction of a space constituting the housing portion 32 compared to the upper side over the step 32A. The step 32A is used for securing and holding the discharge device 1 housed in the housing portion 32.

A connector insertion port 32E open in the left-right direction is formed in the right end portion of the housing portion 32. The connector insertion port 32E allows the inside and the outside of the housing portion 32 to communicate. The connector insertion port 32E is an opening for guiding the feeder connector with respect to the discharge device 1 housed in the housing portion 32.

The housing portion 32 having the above-described shape includes corners 32C and 32F at an edge in contact with the discharge device housing port 32P and an edge of the step 32A, respectively. The corners 32C and 32F each have a shape subject to chamfering, which is commonly performed in machining. In a case where the discharge device 1 includes similar corners (not illustrated), when the discharge device 1 moves in or out of the housing portion 32, the corners of the discharge device 1 may catch on the corners 32C and 32F of the housing portion 32. In a case where the corners of the discharge device 1 catch on the corners 32C and 32F of the housing portion 32, the discharge device 1 may be prevented from moving in or out of the housing portion 32 by the corners 32C and 32F.

The first securing portion 33 protrudes in the left direction from the right upper end portion of the housing portion 32. The first securing portion 33 catches on the discharge device 1 housed in the housing portion 32 to restrict the discharge device 1 from moving outward beyond the first securing portion 33, whereby the discharge device 1 is secured in the housing portion 32.

The second securing portion 34 is disposed on a path when the discharge device 1 is moved in or out of the housing portion 32. The second securing portion 34 is provided to cover, from the outside of the housing portion 32, a section from the vicinity of the left upper end portion of the housing portion 32 to a portion of the discharge device housing port 32P. The second securing portion 34 catches on the discharge device 1 housed in the housing portion 32 to restrict the discharge device 1 from rotational movement about the first securing portion 33, whereby the discharge device 1 is secured in the housing portion 32. When the discharge device 1 is secured by the second securing portion 34 and the first securing portion 33, the discharge device 1 is held in the housing portion 32.

The holder handle 35 is connected to the left end portion of the holder base 31. The holder handle 35 is a portion that allows a user, who is an operator of the electronic apparatus 5 illustrated in FIG. 1, to hold the holder 3. When holding the holder handle 35, the user can insert the housing portion 32 of the holder 3 into the holder insertion port 51C illustrated in FIG. 1 and perform an operation of arranging the housing portion 32 inside the main body 51.

Figure 3:
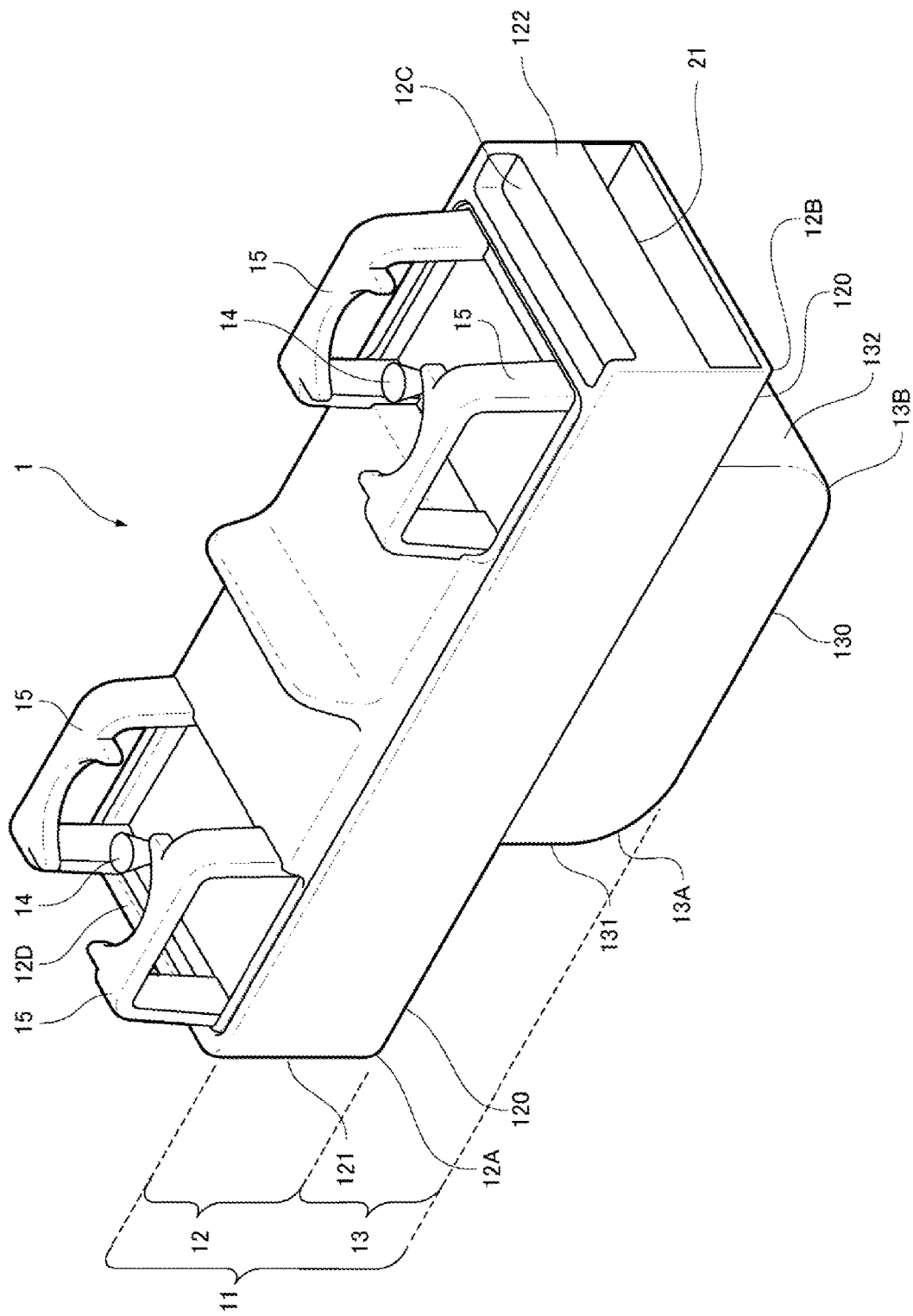
FIG. 3 is a perspective view illustrating the discharge device according to the embodiment of the disclosure.
Figure 4:
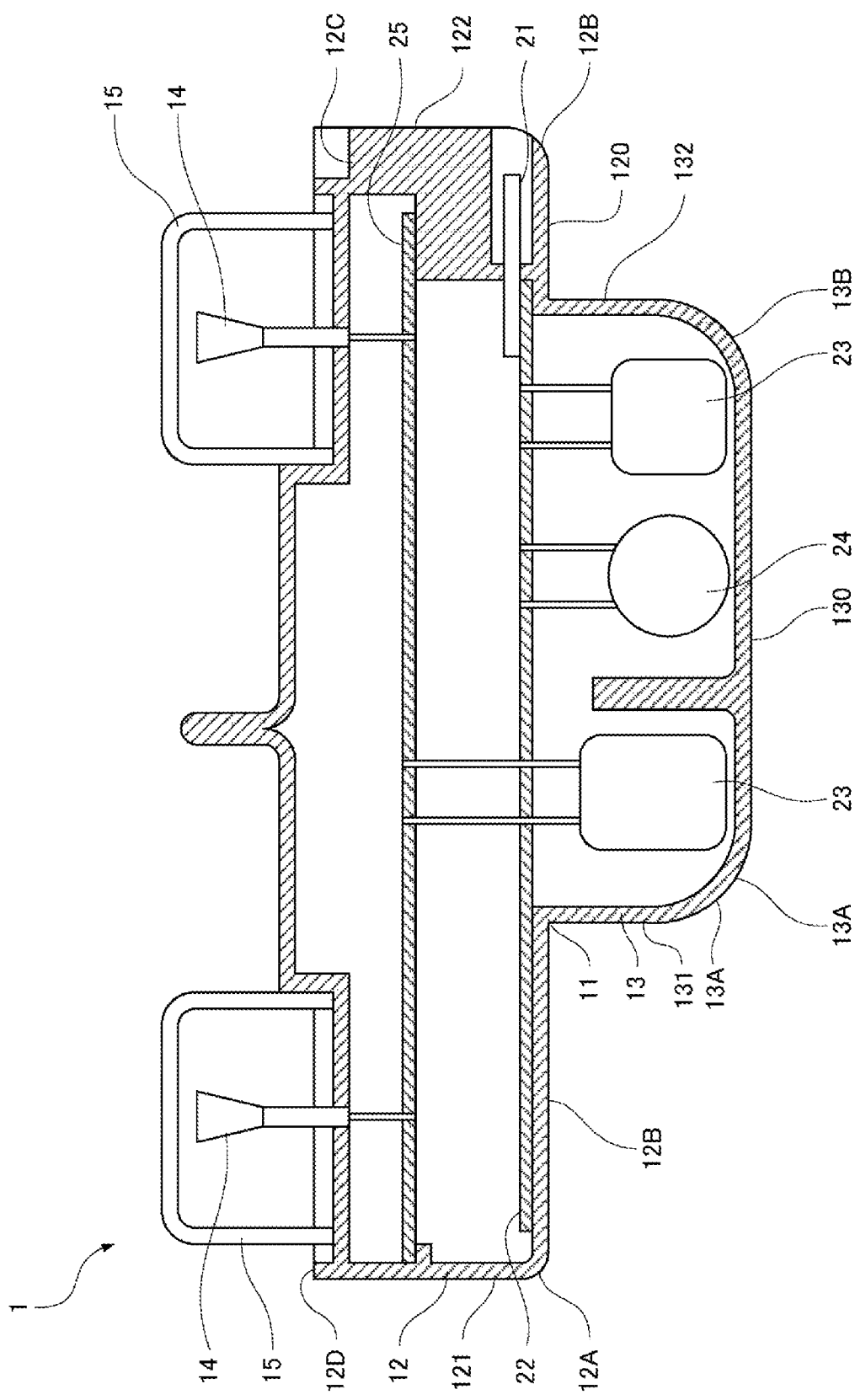
FIG. 4 is a cross-sectional view of the discharge device according to the embodiment of the disclosure.

The discharge device 1 according to the embodiment of the disclosure will be described with reference to FIG. 2 to FIG. 4. FIG. 3 is a perspective view illustrating the discharge device 1 according to the embodiment of the disclosure. FIG. 4 is a cross-sectional view of the discharge device 1 according to the embodiment of the disclosure.

First, the external appearance of the discharge device 1 will be described with reference to FIGS. 2 and 3. As illustrated in FIGS. 2 and 3, the discharge device 1 includes a housed section 11, a discharge electrode 14, and a protector 15.

The housed section 11 is housed in the housing portion 32 such that the discharge electrode 14 is exposed to the outside of the housing portion 32, and is attached to the housing portion 32 by being held by the housing portion 32. The housed section 11 holds the discharge electrode 14 configured to generate a discharge product, and electrical circuit components (not illustrated) configured to operate the discharge electrode 14. The housed section 11 has a box shape. The discharge electrode 14 is provided outside the housed section 11, and the electrical circuit components are housed therein.

The housed section 11 includes a first housed section 12 and a second housed section 13. The first housed section 12 holds the discharge electrode 14. The first housed section 12 is held by the step 32A of the housing portion 32 when housed in the housing portion 32. The second housed section 13 is provided overlapping the first housed section 12. The length of the first housed section 12 in the longitudinal direction is greater than the length of the second housed section 13. The length of the second housed section 13 in the longitudinal direction is preferably smaller than the length, in the longitudinal direction, of a space on the bottom surface 32B side of the housing portion 32 where the step 32A is provided by a predetermined length. With this configuration, when the second housed section 13 moves in or out of the housing portion 32, a space is created between the second housed section 13 and the housing portion 32 in the longitudinal direction of the housing portion 32. As a result, the second housed section 13 moves in or out of the housing portion 32 while avoiding the step 32A in the housing portion 32.

The center of the second housed section 13 in the longitudinal direction is preferably closer to one end portion side of the first housed section 12 in the longitudinal direction relative to the center of the first housed section 12 in the longitudinal direction. Further, when the housed section 11 is housed in the housing portion 32, the second housed section 13 is arranged at a position separate from the step 32A of the housing portion 32 in the longitudinal direction of the housed section 11. With this configuration, when the housed section 11 moves in or out of the housing portion 32, a space is created between the second housed section 13 and the housing portion 32 in the longitudinal direction of the housing portion 32. As a result, the housed section 11 moves in or out of the housing portion 32 while avoiding the step 32A of the housing portion 32.

The second housed section 13 is preferably arranged between both end portions of the first housed section 12 in the longitudinal direction, in the longitudinal direction of the first housed section 12. With this configuration, when the housed section 11 rotates about any position of the first housed section 12 and moves in or out of the housing portion 32, a space is created between the second housed section 13 and the housing portion 32. As a result, the housed section 11 moves in or out of the housing portion 32 while avoiding the step 32A of the housing portion 32 and a surface inside the housing portion 32.

With the first housed section 12 and the second housed section 13 having the above shapes, when the housed section 11 in a tilted orientation with respect to the housing portion 32 is moved in or out of the housing portion 32 while being rotated, the second housed section 13 is housed while avoiding the step 32A of the housing portion 32. Thus, the housed section 11 is housed without catching on the step 32A of the housing portion 32, that is, easily housed.

The first housed section 12 includes a bottom wall 120 and two side walls 121 and 122 opposing each other in the longitudinal direction of the bottom wall 120. At least one of the two side walls 121 and 122 is connected with the bottom wall 120 via a curved surface 12A or 12B. When the first housed section 12 has the above shape and when the corner 32C of the housing portion 32 comes into contact with the curved surface 12A or 12B of the first housed section 12 when the housed section 11 moves in or out of the housing portion 32, the curved surface 12A or 12B of the first housed section 12 guides the corner 32C of the housing portion 32. As a result, the first housed section 12 moves in or out of the housing portion 32 without catching on the corner 32C of the housing portion 32.

Similar to the first housed section 12, the second housed section 13 includes a bottom wall 130 and two side walls 131 and 132 opposing each other in the longitudinal direction of the bottom wall 130. When the second housed section 13 is housed in the housing portion 32, the side wall 131 at one side and the step 32A of the housing portion 32 oppose each other. In the second housed section 13, the bottom wall 130 is connected with the side wall 131 at the one side via a curved surface 13A.

In the second housed section 13, the bottom wall 130 is preferably connected with the side wall 132 at the other side via a curved surface 13B.

The first housed section 12 is provided with a catch portion 12C formed in a recessed shape for catching the first securing portion 33. The catch portion 12C is preferably arranged at a location on a side opposite to the second housed section 13 in the first housed section 12. With this catch portion 12C, the housed section 11 may move in or out of the housing portion 32 while the first securing portion 33 is caught on the catch portion 12C. In this case, the housed section 11 moves in or out of the housing portion 32 by rotating about a contact portion between the catch portion 12C and the first securing portion 33 toward the bottom surface 32B of the housing portion 32. Thus, in a case where the discharge device 1 has to be repeatedly moved in and out of the housing portion 32, the housed section 11 moves in or out of the housing portion 32 by always passing through the same path. After the housed section 11 is housed in the housing portion 32, the discharge device 1 is restricted from moving in a direction toward the first securing portion 33 by maintaining a state in which the first securing portion 33 is caught on the catch portion 12C, whereby the housed section 11 is secured in the housing portion 32.

The discharge electrode 14 is an electrode configured to generate a discharge product, as described above. The discharge electrode 14 is formed of a conductive material such as a metal, carbon fiber, conductive fiber, and conductive resin. The discharge electrode 14 of the present embodiment includes a plurality of linear conductors bundled together to form a brush shape. Note that the shape of the discharge electrode 14 is not limited to a brush shape, and may be any shape such as a rod shape, a needle shape, a linear shape, a fibrous shape, or a plane shape. In the present embodiment, the discharge electrode 14 protrudes from a surface on the side opposite to the surface where the first housed section 12 and the second housed section 13 overlap each other.

A plurality of discharge electrodes 14 are preferably disposed along the longitudinal direction of the housed section 11. When the discharge electrodes 14 are disposed in this manner, it is possible to generate discharge products in amounts corresponding to the number of disposed discharge electrodes 14, and disperse the generated discharge products into the ventilation passage. In the present embodiment, two discharge electrodes 14 are disposed in the first housed section 12 along the longitudinal direction of the first housed section 12.

The protector 15 surrounds the discharge electrode 14 in a state of maintaining a space around the discharge electrode 14 to protect the discharge electrode 14. The protector 15 is provided on a surface of the first housed section 12, from which the discharge electrode 14 protrudes, being spaced from one end portion of the housed section 11 in the longitudinal direction. When the protector 15 has the configuration described above, the second securing portion 34 can be disposed to catch on a portion of the first housed section 12 between an end portion of the first housed section 12 and the protector 15. The second securing portion 34 caught on the first housed section 12 restricts the rotational movement of the first housed section 12 about the contact portion between the first securing portion 33 and the catch portion 12C. As a result, the first housed section 12 is secured in the housing portion 32. Hereinafter, a portion of the first housed section 12 between the end portion of the first housed section 12 and the protector 15 is referred to as a secured portion 12D.

Next, the interior of the discharge device 1 will be described with reference to FIG. 4. As illustrated in FIG. 4, the discharge device 1 includes a connection portion 21, a control substrate 22, a step-up transformer 23, a capacitor 24, and a high voltage substrate 25.

The connection portion 21 connects the electrical circuit components including the discharge electrodes 14 to an external power supply via a feeder connector provided inside the main body 51. The connection portion 21 is connected to the electrical circuit components housed inside the housed section 11, and part of the connection portion 21 is exposed to the outside of the housed section 11. The part of the connection portion 21 exposed to the outside of the housed section 11 is connected to the feeder connector. The connection portion 21 is provided at a position in parallel to the catch portion 12C in the housed section 11. The connection portion 21 is provided between the curved surface 12B, connecting the bottom wall 120 and the side wall 122 of the first housed section 12, and the catch portion 12C in the first housed section 12. With the connection portion 21 having the above arrangement, when the housed section 11 rotates and moves in or out of the housing portion 32 while the catch portion 12C is caught on the first securing portion 33, the connection portion 21 moves without catching on the bottom surface 32B or the corners 32C and 32F of the housing portion 32. Thus, the housed section 11 can move in or out of the housing portion 32 with ease.

The control substrate 22 has a wide shape and is housed in the first housed section 12. The control substrate 22 is connected to the connection portion 21. A voltage is applied to the control substrate 22 from the feeder connector via the connection portion 21. The step-up transformer 23, the capacitor 24, and the electrical components (not illustrated) are mounted on the control substrate 22. The control substrate 22 is connected to the high voltage substrate 25.

The step-up transformer 23 is a component that boosts a voltage, and has a large depth dimension and large height dimension. The second housed section 13 preferably houses the step-up transformer 23. With this configuration, the second housed section 13 needs to have a height sufficient for housing the step-up transformer 23, but the length of the second housed section 13 in the longitudinal direction may be made smaller than the length of the first housed section 12, as described above. Thus, as described above, the housed section 11 can move in or out of the housing portion 32 without catching on the step 32A of the housing portion 32. In the present embodiment, two step-up transformers 23 having differing amplification factors, shapes, and the like are housed in the second housed section 13. The two step-up transformers 23 are mounted on the control substrate 22 and the high voltage substrate 25, respectively. The step-up transformer 23 corresponds to an example of a "high voltage generation component" of the disclosure.

The capacitor 24 has a function of temporarily storing voltage from the step-up transformer 23. The capacitor 24 is also a component having a large depth dimension and large height dimension, similar to the step-up transformer 23. The second housed section 13 preferably houses the capacitor 24. With this configuration, the length of the second housed section 13 in the longitudinal direction may be made smaller than the length of the first housed section 12, as described above. Thus, as described above, the housed section 11 can move in or out of the housing portion 32 without catching on the step 32A of the housing portion 32. The capacitor 24 corresponds to an example of the "high voltage generation component" of the disclosure.

The high voltage substrate 25 plays a role of supplying a desired high voltage obtained by the step-up transformer 23, the capacitor 24, and the various electrical components (not illustrated) to the discharge electrode 14. The high voltage substrate 25 has a wide shape and is housed in the first housed section 12.

Figure 5A:
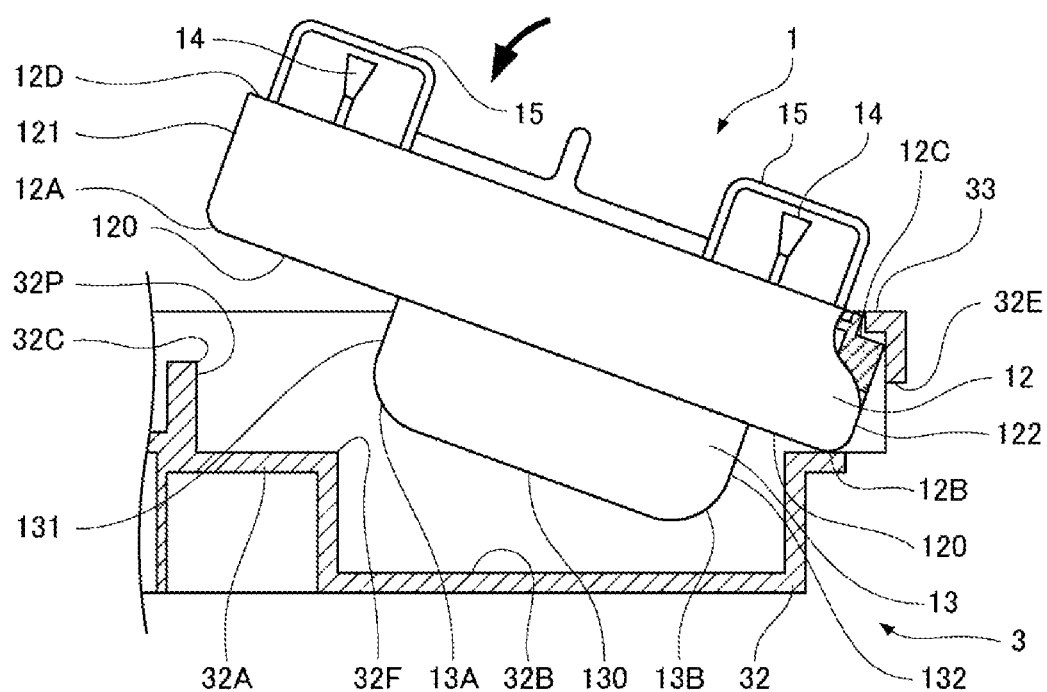
FIG. 5A is a diagram illustrating a preliminary stage of attachment of the discharge device according to the embodiment of the disclosure to the holder.
Figure 5B:
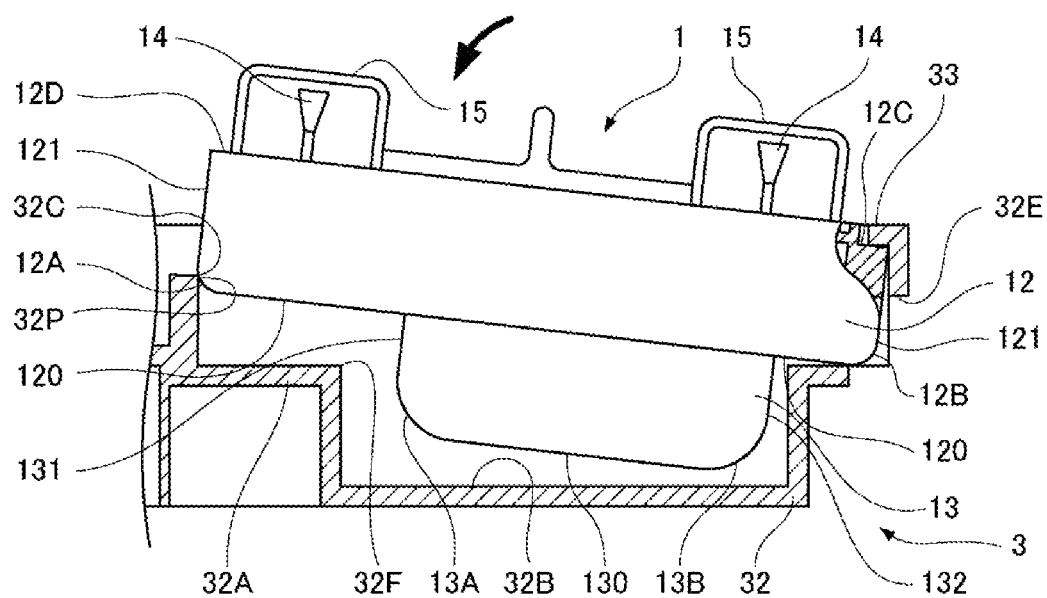
FIG. 5B is a diagram illustrating a mid-stage of attachment of the discharge device according to the embodiment of the disclosure to the holder.
Figure 5C:
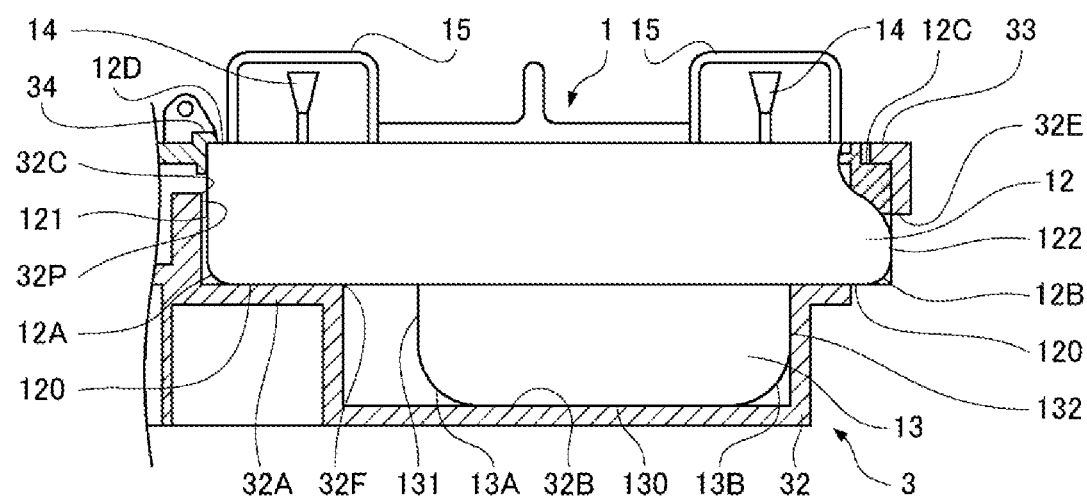
FIG. 5C is a diagram illustrating a final stage of attachment of the discharge device according to the embodiment of the disclosure to the holder.

Attachment of the discharge device 1 according to the embodiment of the disclosure to the holder 3 will be described with reference to FIG. 5A to FIG. 5C. FIG. 5A is a diagram illustrating a preliminary stage of the attachment of the discharge device 1 according to the embodiment of the disclosure to the holder 3. FIG. 5B is a diagram illustrating a mid-stage of the attachment of the discharge device 1 according to the embodiment of the disclosure to the holder 3. FIG. 5C is a diagram illustrating a final stage of the attachment of the discharge device 1 according to the embodiment of the disclosure to the holder 3.

The discharge device 1 illustrated in FIG. 5A is housed in the housing portion 32 of the holder 3, and is then attached to the holder 3 by being secured in the housing portion 32. In order to make the discharge device 1 be housed in the housing portion 32, the discharge device 1 is rotated such that the bottom wall 130 of the second housed section 13 faces the bottom surface 32B of the housing portion 32 while the catch portion 12C is caught on the first securing portion 33.

When the rotation of the discharge device 1 is advanced, the curved surface 13B of the second housed section 13 opposes the bottom surface 32B of the housing portion 32. The shape of the curved surface 13B serves to avoid the bottom surface 32B of the housing portion 32. Even when the curved surface 13B comes into contact with the bottom surface 32B of the housing portion 32, the curved surface 13B does not catch on the bottom surface 32B of the housing portion 32 due to its shape. This makes it possible for the housed section 11 to move in or out of the housing portion 32 with ease.

The curved surface 13A opposes the step 32A provided inside the housing portion 32. The shape of the curved surface 13A serves to avoid the corner 32F of the step 32A, or avoid the step 32A itself. Thus, the housed section 11 moves without catching on the step 32A of the housing portion 32.

As illustrated in FIG. 5B, when the rotation of the discharge device 1 is further advanced, the curved surface 12A of the first housed section 12 opposes the corner 32C of the housing portion 32, which is in contact with the discharge device housing port 32P. The curved surface 12A moves without coming into contact with the corner 32C of the housing portion 32 due to its shape. Even when the curved surface 12A of the first housed section 12 comes into contact with the corner 32C of the housing portion 32, the curved surface 12A of the first housed section 12 guides the corner 32C of the housing portion 32, and thus the first housed section 12 moves without catching on the corner 32C of the housing portion 32.

When the rotation of the discharge device 1 is further advanced, the discharge device 1 is housed in the housing portion 32. As described above, the discharge device 1 moves without catching on the corner 32C of the housing portion 32 in the process of being attached to the housing portion 32. That is, the discharge device 1 is easily housed in the holder 3.

As illustrated in FIG. 5C, the discharge device 1 housed in the housing portion 32 is restricted from moving in a direction beyond the first securing portion 33 by the first securing portion 33, and only movement in a rotational direction about the first securing portion 33 is allowed. The movement of the discharge device 1 in the rotational direction is restricted by a simple operation of causing the second securing portion 34 to catch on the secured portion 12D of the first housed section 12. That is, the discharge device 1 is easily secured by the second securing portion 34.

As described above, the discharge device 1 of the embodiment of the disclosure can be easily housed in the holder 3, and can also be easily secured in the holder 3. That is, the discharge device 1 of the embodiment of the disclosure can be easily attached to the holder 3.

The embodiments of the disclosure have been described above with reference to the accompanying drawings. However, the disclosure is not limited to the embodiments described above, and the disclosure can be implemented in various modes without departing from the gist thereof. For ease of understanding, the drawings schematically illustrate each component as a main constituent, and the thickness, length, number, spacing, and the like of each component illustrated are different from the actual thickness, length, number, and spacing for convenience of drawing preparation. Further, the material, shape, dimensions, and the like of each component described in the embodiments described above are examples and are not particularly limited, and various modifications can be made within a range that does not substantially deviate from the configuration of the disclosure.

INDUSTRIAL APPLICABILITY

The disclosure provides a discharge device, and the provided discharge device has industrial applicability.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A discharge device to be housed in a housing portion of a holder, the discharge device comprising:
    a housed section to be housed in the housing portion; and
    a discharge electrode protruding from the housed section,
    wherein the housed section includes
    a bottom wall, and
    two side walls opposing each other in a longitudinal direction of the bottom wall,
    at least one of the two side walls is connected with the bottom wall via a curved surface, and
    the curved surface guides a corner of the housing portion at a time of housing the housed section in the housing portion such that the housed section is housed in the housing portion without catching on the corner.

2. The discharge device according to claim 1,
    wherein the housing portion has a step structure,
    the housed section includes a first housed section from which the discharge electrode protrudes, and a second housed section overlapping the first housed section,
    a length of the first housed section in a longitudinal direction is greater than a length of the second housed section in a longitudinal direction, and
    the second housed section avoids a step of the housing portion at a time of housing the housed section while changing an orientation of the housed section from a tilted orientation to an orientation suitable for housing.

3. The discharge device according to claim 2,
    wherein a center of the second housed section in the longitudinal direction is closer to one end portion side of the first housed section in the longitudinal direction relative to a center of the first housed section in the longitudinal direction.

4. The discharge device according to claim 2,
    wherein the second housed section is arranged between both end portions of the first housed section in the longitudinal direction, in the longitudinal direction of the first housed section.

5. The discharge device according to claim 2,
    wherein the second housed section includes one of the curved surfaces.

6. The discharge device according to claim 2,
    wherein the second housed section includes two of the curved surfaces at different positions in the longitudinal direction.

7. The discharge device according to claim 2,
    wherein the second housed section houses a high voltage generation component configured to supply a high voltage to the discharge electrode.

8. The discharge device according to claim 1,
    wherein the holder includes a first securing portion,
    the first securing portion protrudes from the housing portion toward a path through which the housed section passes at a time of moving in or out of the housing portion,
    the housed section includes a catch portion formed in a recessed shape for catching the first securing portion,
    the housed section is housed in the housing portion by rotating with the catch portion catching on the first securing portion, and
    at a time of housing the housed section in the housing portion, the first securing portion catches on the catch portion of the housed section to secure the housed section.

9. The discharge device according to claim 8, further comprising:
    a connection portion configured to connect electrical circuit components including the discharge electrode to an external power supply,
    wherein the connection portion is provided at a position in parallel to the catch portion in the housed section.

10. The discharge device according to claim 1,
    wherein a plurality of the discharge electrodes are disposed along the longitudinal direction of the housed section.

11. The discharge device according to claim 10,
    wherein the housing portion includes a second securing portion,
    the discharge device further includes a protector surrounding the discharge electrode in a state of maintaining a space around the discharge electrode to protect the discharge electrode, and the protector is provided spaced apart from one end portion of the housed section in the longitudinal direction, and the second securing portion is caught in the housed section between the one end portion of the housed section and the protector to secure the housed section.

\* \* \* \* \*